United States Patent [19]

Norris et al.

[11] Patent Number: 5,824,519
[45] Date of Patent: Oct. 20, 1998

[54] TISSUE-SPECIFIC AND TARGET RNA-SPECIFIC RIBOZYMES

[75] Inventors: James S. Norris, Mt. Pleasant, S.C.; Gary A. Clawson, Hershey, Pa.

[73] Assignee: Medical University of South Carolina, Charleston, S.C.

[21] Appl. No.: 554,369

[22] Filed: Nov. 8, 1995

[51] Int. Cl.$^6$ .............................. C12P 19/34; C12N 15/11; C07H 21/02
[52] U.S. Cl. .................................. 435/91.31; 435/320.1; 536/24.5
[58] Field of Search .............................. 435/91.31, 320.1, 435/375, 172.1, 172.3; 514/44; 536/23.1, 24.1, 24.5, 25.1; 935/33, 34, 36

[56] References Cited

U.S. PATENT DOCUMENTS

| | | | |
|---|---|---|---|
| 5,436,330 | 7/1995 | Taira et al. | 536/23.2 |
| 5,500,357 | 3/1996 | Taira et al. | 435/91.31 |

FOREIGN PATENT DOCUMENTS

| | | |
|---|---|---|
| 0 640 688 A1 | 12/1988 | European Pat. Off. . |
| WO 92/10590 | 6/1992 | WIPO . |
| WO 94/03594 | 2/1994 | WIPO . |

OTHER PUBLICATIONS

Gewirtz et al. "Facilitating oligonucleotide delivery: Helping antisense delivery on its promis" Proc. Natl. Acad. Sci. USA 93: 3161–3163, Apr. 1996.

Stull et al. "Antigene, ribozyme and aptamer nucleic acids drugs: Progress and Prospects" Pharm. Res. 12(4): 465–483, Apr. 1995.

Usman et al. "Design, synthesis, and function of therapeutic hammerhead ribozymes" Nucleic acids and Biology 10: 243–264, 1996.

Database WPI, Section Ch, Week 9335 Derwent Publications Ltd., London, GB; Class B04, AN 93–277467, XP002026580 and JP 05 192 151 A (Agency of Ind Sci & Technology), 3 Aug. 1993 Abstract.

Vieweg et al., "Efficient Transfer with Adeno–associated Virus–based Plasmids Complexed . . . Human Prostate Cancer" *Cancer Res.* 55:2366–2372, Jun., 1995.

Greenberg et al. "The Rat Probasin Gene Promoter Directs Hormonally and Developmentally . . . Transgenic Mice" *Mol. Endo.* 8(2):230–239, 1994.

Whitton, J. Lindsay "Antisense Treatment of Viral Infection" *Adv. in Virus Res.* 44:267–303, 1994.

Castanotto et al. "Antisense Catalytic RNAs as Therapeutic Agents" *Adv. in Pharmacol.* 25:289–317, 1994.

Yuyama et al. "Construction of a tRNA–embedded–ribozyme trimming plasmid" *Biochem. and Biophy. Res. Comm.* 186(3):1271–1279, Aug. 14, 1992.

Taira et al. "Construction of a novel RNA–transcript–trimming plasmid which can be used both . . . transcription vectors" *Nuc. Acids Res.* 19(19)5125–5130, 1991.

Ohme–Takagi et al. In vivo RNA transcript–releasing plasmid possessing a universal . . . artificial ribozymes *Nuc. Acids Symp. Ser.* No. 22, 49–50, Oxford Univ. Press, Oxford, England 1990.

Taira et al. "Construction of a novel artificial–ribozyme–releasing plasmid" *Protein Eng.* 3(8):733–737, 1990.

*Primary Examiner*—George C. Elliott
*Assistant Examiner*—Thomas G. Larson
*Attorney, Agent, or Firm*—Needle & Rosenberg, PC

[57] ABSTRACT

The invention provides tissue-specific and target RNA-specific ribozymes. These ribozymes can be used to destroy target-specific neoplasms and to treat viral infections, among other uses. The ribozymes of the present invention comprise a 5' autocatalytically cleaving ribozyme sequence, a catalytic ribozyme comprising a target RNA-specific binding site and a 3' autocatalytically cleaving ribozyme. The invention also provides nucleic acids which encode the ribozymes of the invention. These nucleic acids can be used to express the ribozymes of the invention at the selected site. Methods of treating disease by administering the ribozymes are provided.

16 Claims, 3 Drawing Sheets

FIG. 1

GCGGCCGC TC GAG CTC TGA TGA GTC CGT GAG GAC GAA ACG GTA CCC
    1                                                20

GGT ACC GTC AGC TCG AGC TC AGATCT GGA TCC GTC GAC GGA TCT AGA
 40                                       60                                   80

TCC GTC CTG ATG AGT CCG TGA GGA CGA AAC GGA TCT GCA GCGGCCGC
                   100                                          120

FIG. 2

GCGGCCGC TC GAG CTC TGA TGA GTC CGT GAG GAC GAA ACG GTA CCC GGT ACC
1                               20                              40

GTC AGC TCG AGC TC AGATCT TTC AAA GAC TGA CTC GCT GAG GAC GAA ACG
                    60                          80

AGG ATC AGATCT GGA TCC GTC GAC GGA TCT AGA TCC GTC CTG ATG AGT CCG TGA
100                         120                         140

GGA CGA AAC GGA TCT GCA GCGGCCGC
160

TISSUE-SPECIFIC AND TARGET RNA-SPECIFIC RIBOZYMES

BACKGROUND OF THE INVENTION

1. Field of the Invention

The invention pertains to the use of tissue-specific and target RNA-specific ribozymes for treatment of cancers and bacterial, parasitic and viral infections. More specifically, the invention relates to a ribozyme targeted to the RNA polymerase 1(A) under the control of the probasin promoter.

2. Background Art

A ribozyme is a catalytic RNA molecule that cleaves RNA in a sequence specific manner. The use of ribozyme as potential gene regulators in mammalian cells and antiviral agents has been suggested, but subject to serious questions regarding technical feasibility. For example, it is not known how ribozymes can be introduced to target cells or how they can be directed to the same subcellular compartments as their target RNAs. Other questions concern the effects of target RNA secondary structure on ribozymal activity. The art has not been successful in answering any of these questions.

Furthermore, because ribozymes are a form of antisense technology, the problems encountered in applying antisense technology to disease treatment are also encountered in the use of ribozyme technology. For example, it has been shown that the expression of antisense RNA in transgenic mice did not invariably lead to a reduction in target RNA molecules, and when reduction in target RNA molecules did occur, it was not predictably paralleled by a reduction in protein. Even when protein levels were reduced sometimes no biological effect was detected (Whitton, J. Lindsay "Antisense Treatment of Viral Infection" *Adv. in Virus Res.* Vol. 44, 1994).

The experience in the art suggests that it is also not clear whether ribozymes work best when free, or when embedded in an unrelated large RNA molecule (Whitton, 1994). At present, sufficient data are not available, either in vitro or in cell culture to allow systematic comparison of the transactivities of free ribozymes with their embedded equivalents.

There have been some studies that focus on the potential use of ribozyme technology in the treatment of cancer. In these studies, ribozymes have been directed against both c-fos and c-ras oncogenes in cell culture and showed some suppression of the malignant potential of cells when transplanted into mice. Nevertheless, these ribozymes specifically target an oncogene.

There has been no suggestion in the literature that tissue-specific cancers or other tissue-specific disease can be treated by delivering to that tissue a ribozyme having a tissue-specific promoter, and that it is targeted to an RNA that is essential for cell survival. The invention provides such a ribozyme capable of treating tissue-specific cancers and other tissue-specific diseases.

The magnitude of the prostate cancer problem requires little introduction. Approximately 44,000 men die each year of prostate cancer and about 10,000,000 men have precancerous conditions of the prostate. It is clear that new approaches to therapy are needed. Animal models for testing therapeutic approaches are just becoming available, and will require a number of years for validation. However, the present invention provides important reagents to address this problem.

One of the difficulties in using gene therapy to treat prostate cancer is the long standing problem of target-specific delivery. However, the recently developed probasin promoter provides target-specificity enabling systemic delivery of the present ribozyme-encoding vector (Greenberg et al. *Mol. Endocrinol.* 8:230–239, 1994). The present vector consists of a tandem array of 3 hammerhead ribozymes, the 5' and 3' of which are designed to autocatalytically cleave themselves from the primary transcript. This novel construct eliminates problems inherent with extensive residual flanking sequences which might otherwise be present to compromise catalytic activity and specificity. The present constructs couple the prostate specific probasin promoter to triple-ribozymes targeted at mRNAs critical for prostate cell growth.

Endogenous delivery of a ribozyme under the control of a tissue-specific or other promoter can be complicated by "leakiness", where low levels of transcription occur in extraneous tissues. This could present a considerable therapeutic problem, depending upon the cellular target chosen. The present ribozyme compensates for this problem by targeting a cellular target which is associated with high levels of product (that is, RNA polymerase I produces large amounts of cellular ribosomal RNA). Thus, in the event promoter leakiness occurs in unintended tissues, it is not likely that cell death would occur. This choice, therefore, provides a needed level of safety, and targeting of pol I would be applicable to many selected tissues using other promoters.

A common problem in gene therapy is the difficulty in delivering the ribozyme to the correct tissue. The present invention avoids this difficulty by targeting the ribozyme to non-cellular RNAs in cells to which ribozyme constructs can be efficiently delivered. IV liposome delivery will be effective for treatment of HBV hepatitis. IV and/or extracorporeal treatment will effectively delivery construct to erythrocytes for treatment of malarial infection. And topical (with or without iv) administration will effectively deliver ribozyme construct to cervical epithelium in dysplastic/precancerous/cancerous HPV 16 cervical lesions. This latter example is of extreme importance for treatment of dysplastic/carcinoma in situ lesions diagnosed via abnormal Pap smears. A second advantageous facet of the non-cellular target ribozymes is that even if promoter leakiness and/or extraneous delivery and/or expression of the ribozyme occurs in unintended cells, the ribozymes should not cleave any cellular RNAs.

SUMMARY OF THE INVENTION

The invention provides tissue-specific and target RNA-specific ribozymes. These ribozymes can be used to destroy target-specific neoplasms and to treat viral infections, among other uses. The ribozymes of the present invention comprise a 5' autocatalytically cleaving ribozyme sequence, a catalytic ribozyme comprising a target RNA-specific binding site and a 3' autocatalytically cleaving ribozyme.

The invention also provides nucleic acids which encode the ribozymes of the invention. These nucleic acids can be used to express the ribozymes of the invention at the selected site. The nucleic acids of the invention comprise a tissue-specific promoter binding site upstream from a sequence encoding a 5' autocatalytically cleaving ribozyme sequence, a catalytic ribozyme comprising a target RNA-specific binding site and a 3' autocatalytically cleaving ribozyme sequence.

A method of treating a subject having a proliferative disease of a specific tissue by inhibiting cell proliferation in the tissue, comprising administering to the subject the ribozyme-encoding construct of the present invention, wherein the target-specific promoter binding sequence is specific for the diseased tissue, whereby the ribozyme encoded by the nucleic acid is expressed, ribosomal RNA production in the tissue is inhibited, cell proliferation is inhibited, and the proliferative disease treated is provided.

A method is provided for treating a subject having prostate cancer, comprising administering to the subject the ribozyme-encoding construct of the present invention, whereby the ribozyme encoded by the nucleic acid is expressed in the prostate and the prostate cancer is treated.

A method of treating an infection in a subject, comprising administering to the subject the ribozyme-encoding construct of the present invention, wherein the encoded target RNA-specific binding site is specific for an RNA unique to the infectious agent, whereby the ribozyme encoded by the nucleic acid is expressed and the infectious agent is killed is also provided.

BRIEF DESCRIPTION OF THE FIGURES

FIG. 1 shows DNA encoding the parental double ribozyme starting at Not I site. This sequence is shown within SEQ ID NO:1. Underlined sequences are Not I sites (GCGGCCGC) and Bgl II (AGATCT).

FIG. 2 shows DNA encoding the entire sequence with the internal Pol I targeted triple ribozyme in bold. This sequence is shown in SEQ ID NO:1. Underlined sequences are Not I (GCGGCCGC) and Bgl II (AGATCT).

DETAILED DESCRIPTION OF THE INVENTION

Ribozymes

Figure 3:
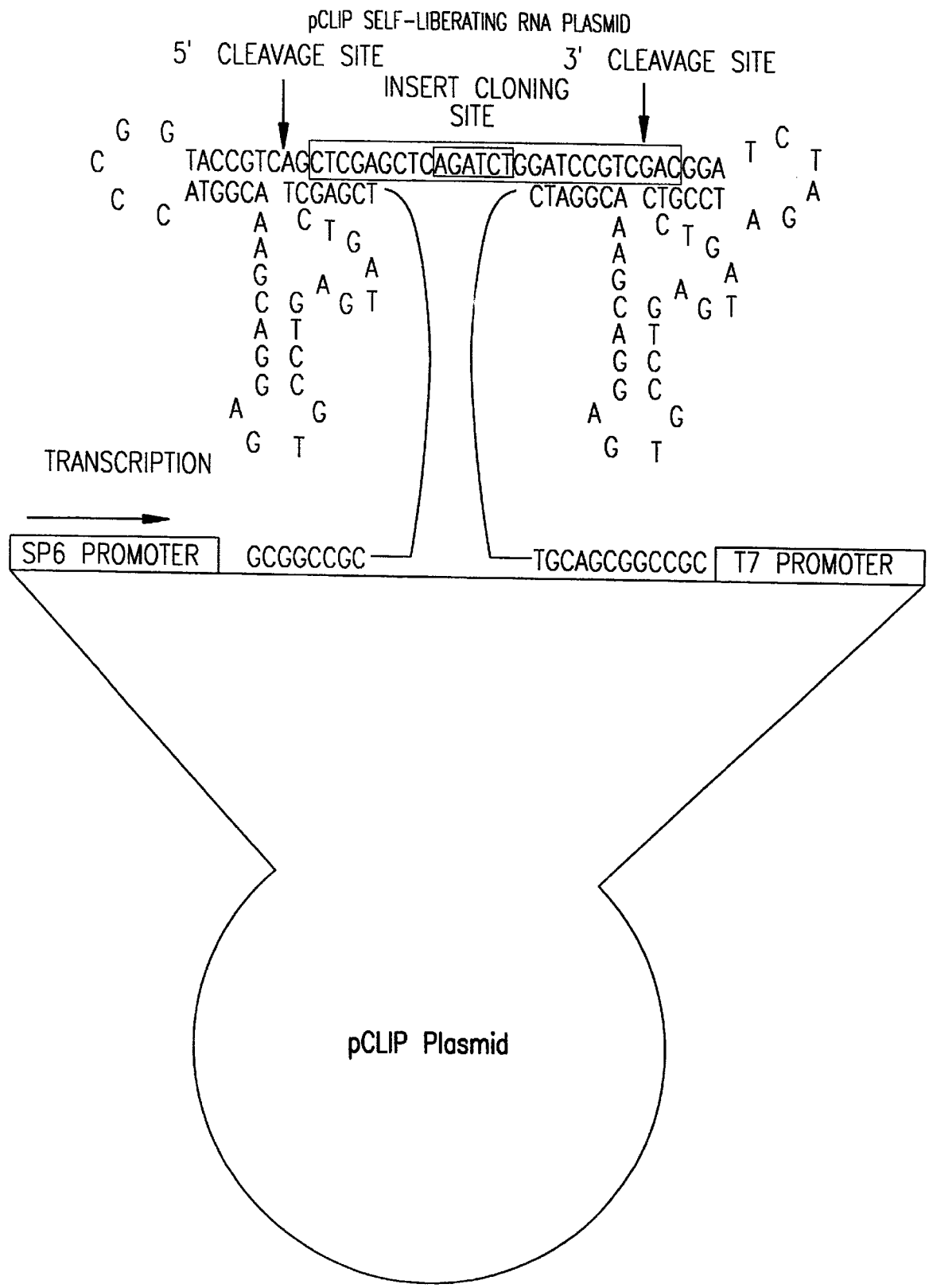
FIG. 3 shows the two dimensional structure of parent double ribozyme into which the core ribozyme was cloned, as its reverse complement DNA. This sequence is shown in SEQ ID NO:1.

The invention provides tissue-specific and target RNA-specific ribozymes. These ribozymes can be used to destroy tissue-specific neoplasms and to treat viral, bacterial or parasitic infections, among other uses. The ribozymes of the present invention comprise a 5' autocatalytically cleaving ribozyme sequence, a catalytic ribozyme comprising a target RNA-specific binding site and a 3' autocatalytically cleaving ribozyme. One example of the present ribozyme is shown in by its DNA coding sequence in FIG. 2 and in SEQ ID NO:1. The nucleotides numbered 1–164 encode the ribozyme, including the 5' and 3' autocatalytic ribozyme sequences. The 5' autocatalytically cleaving ribozyme, catalytic ribozyme, and 3' autocatalytically cleaving ribozyme of this exemplary ribozyme are shown separately in SEQ ID No:1.

Alternatively, the 5' autocatalytically cleaving ribozyme can be replaced with another stretch of transcribed RNA. In this RNA, the first 20–30 nt (or longer) are followed by a sequence which represents the reverse complement of the initial 20–30 nt. This way, the construct would presumably still be capped at the 5' end the way pol II transcripts are, but the initial nucleotides should not alter the specificity of the nucleotides on the 5' side of the targeted middle ribozyme. Based upon the fact that the transcript would be capped, it should be exported efficiently to the cytoplasm. For present triple ribozyme construct having both 5' and 3' autocatalytic ribozymes, it is expected that there will be some diffusion mediated transport to the cytoplasm of the internal targeted ribozyme, although this alternative 5' end should increase the cytoplasmic proportion.

The invention provides ribozymes that have the unique characteristic of being both target RNA-specific in their catalytic action, and subject to tissue-specific expression. In the example shown in FIG. 1 and SEQ ID NO:1, the target RNA specificity is conferred by an RNA binding site that specifically binds a sequence that is unique to RNA polymerase I(A) (ribosomal RNA polymerase). It will be understood that an RNA sequence unique for any RNA can be the target of the present target RNA-specific ribozyme. The determination of unique sequences is routine given the availability of numerous computer databases (GenBank) and computer programs (Genetics Computer Group, PCGENE and BLAST) which can search for and find any matches between nucleic acid sequences. A unique DNA sequence located on one of the databases will have a corresponding unique RNA sequence.

One example of the catalytic sequence of the present ribozymes is also shown as its DNA coding sequence in FIG. 1 and SEQ ID NO:1. Other catalytic sequences include those known in the art. A number of sequence variation have defined permissible nucleotide alteration in "stem" regions (Fedor and Uhlenbeck *Proc. Nat. Acad. Sci.* 87:1668–1672, 1990). Those skilled in the art will understand that any catalytic sequence, even those not yet discovered, can be used to construct a ribozyme of the invention when it is routinely combined with the autocatalytically cleaving ribozymes and RNA binding site as described herein.

One example of the 5' and 3' autocatalytically cleaving ribozymes that are expressed with the catalytic ribozyme of the invention are shown in FIG. 1 and SEQ ID NO:1, and also in FIGS. 2 and 3. As further described below, these ribozymes are important for the expression of the catalytic ribozyme, because they cleave off of the ribozyme transcript as soon as they are transcribed to produce a catalytic ribozyme having minimal extraneous 5' or 3' sequences. Thus, the target-specific binding site and the catalytic sequence that comprise the catalytic ribozyme are in the correct configuration to bind and cleave the target RNA. The extraneous sequences in the exemplified construct are the result of the cloning procedure. It is understood that with the selection of an alternative cloning scheme some or all of these extraneous nucleotides can be eliminated.

Ribozyme Encoding Nucleic Acids

The invention also provides nucleic acids which encode the ribozymes of the invention. These nucleic acids can be used to express the ribozymes of the invention at the selected site. The site can be tissue-specific in the case of treating tissue-specific cancers, or it can be target-specific in the case of ribozymes that prevent replication of infectious agents to treat infection (e.g. hepatitis, herpes, malaria, tuberculosis, etc.).

The nucleic acids of the invention comprise a tissue-specific promoter binding site upstream from a sequence encoding a 5' autocatalytically cleaving ribozyme sequence, a catalytic ribozyme comprising a target RNA-specific binding site and a 3' autocatalytically cleaving ribozyme sequence.

The tissue-specific promoter binding site in the ribozyme-producing construct results in tissue-specific expression of the ribozyme in tissue(s) that actively transcribe RNA from the selected promoter. Thus, only the target RNA in tissue that utilizes the promoter will be cleaved by the ribozyme. The exemplary ribozyme shown in FIG. 1 and SEQ ID NO:1 uses the binding site for the probasin promoter, a promoter-specific for prostate epithelium (Greenberg et al., 1994). This tissue-specific promoter binding site has the sequence shown in (Greenburg et al., 1994).

As expected, other tissue-specific promoters can be used in the present nucleic acid constructs. Examples of these promoters include the binding sites for prostate-specific antigen (prostate), albumin (liver), fatty acid binding protein (ilium), whey acidic protein (breast), smooth muscle actin (smooth muscle), etc. It will also be clear that target-specific promoters not yet identified can be used to target expression of the present ribozymes to the selected tissue(s). Once a target-specific promoter is identified its binding sequence can be routinely determined by routine methods such as sequence analysis. The promoter is defined by deletion analysis, mutagenesis, footprinting, gel shifts and transfection analyses (Sambrook et al., *Molecular Cloning: A Laboratory Manual*, 2nd Ed., Cold Spring Harbor Laboratory, Cold Spring Harbor, N.Y., 1989).

In the ribozyme-encoding nucleic acid of the invention, the nucleic acid encoding the 5' autocatalytically cleaving ribozyme can have the sequence of nucleotides 1–54 shown in SEQ ID NO:1. In the ribozyme-encoding nucleic acid of the invention, the nucleic acid encoding the 3' autocatalytically cleaving ribozyme can have the sequence of nucleotides 111–164 shown in SEQ ID NO:1.

It is understood that other 5' and 3' autocatalytically cleaving ribozymes may be developed that can be encoded by the present nucleic acids. These ribozymes can be developed according to the methods of Taira et al. (*Nuc. Acids Res.* 19(19):5125–5130, 1991).

The present nucleic acid encodes a catalytic ribozyme that contains two separable functional regions: a highly conserved catalytic sequence which cleaves the target RNA (also known as the "catalytic core"), and flanking regions which include a target RNA-specific binding site. By nucleic acid complementarity, the binding site directs the ribozyme core to cleave a specific site on the target RNA molecule. The length of flanking sequences have implications not only for specificity, but also for the cleavage efficiency of the individual ribozyme molecules. In the present catalytic ribozyme, the flanking sequences are highly specific for the target RNA, yet allow ready dissociation from the target RNA once cleavage occurs. This permits cycling of the ribozyme (with an expected $K_{cat}$ of about 1 cleavage per minute) and reduces the amount of ribozyme required to be effective. A range of binding/dissociation values from 16–21 Kcal should be effective.

The complexity of human RNA is about 100 fold lower than that for human DNA, and specificity can be achieved with as few as 12–15 base pairs. The stability of the RNA—RNA duplex is effected by several factors, such as GC content, temperature, pH, ionic concentration, and structure. The nearest neighbor rules can provide a useful estimate of the stability of the duplex (Castanotto et al. "Antisense Catalatic RNAs as Therapeutic Agents" *Advances in Pharmacol.* 25:289–317, 1994).

As described above, the encoded RNA binding site is unique, so the encoding nucleic acid sequence will be the corresponding unique DNA sequence. The RNA binding site can comprise a sequence that binds to an RNA sequence unique to ribosomal RNA polymerase I(A) subunit. The ribosomal RNA polymerase binding site encoding DNA can have the sequence shown in FIG. 3. This is a sequence from the RNA polymerase I(A) subunit.

The catalytic ribozyme of the invention also includes a catalytic sequence, which cleaves the target RNA near the middle of the site to which the target RNA-specific binding site binds. In the hammerhead type of ribozyme, the catalytic sequence is generally highly conserved. The conserved catalytic core residues are 5' CUGANGA 3' and 5' GAAA 3' linked by an evolutionarily conserved stem-loop structure.

The most conserved and probably most efficiently cleaved sequence on the target RNA is 5' GUC 3'. However, XUN (N=A, U or C) can also be cleaved efficiently. Such cleavage sites are ubiquitous in most RNAs allowing essentially all RNA's to be targeted (Whitton, J. Lindsay "Antisense Treatment of Viral Infection" *Adv. in Virus Res.* Vol. 44, 1994).

With regard to the selection of the appropriate sites on target RNA, it is known that target site secondary structure can have an effect on cleavage in vitro (Whitton, 1994). Thus, the selected target molecule's sequence can be routinely screened for potential secondary structure, using the program RNAFOLD (from the PCGENE group of programs or available on the Internet). Thus, reasonable predictions of target accessibility can be made. Computer assisted RNA folding (Castanotto et al., 1994), along with computational analysis for 3-dimensional modeling of RNA (Major et al., *Science* 253:1255–1260, 1991 and Castanotto et al., 1994) is certainly effective in guiding the choice of cleavage sites.

The internal ribozyme can be targeted to noncellular RNAs necessary for growth of parasites, virus life cycles, etc., and expression can be driven with tissue-specific or virus-specific promoters. Three important examples which are specifically presented in the application are:

A) Use of the albumin promoter with a Hepatitis B virus target (chosen to cleave the viral RNA pregenome, S protein, and polymerase/reverse transcriptase transcripts using the same ribozyme target site);

B) Use of generic promoters active in erythrocytes, using a ribozyme targeted to highly conserved regions of the EMP-1 protein family from *P. falciparum,* which are necessary for cytoadherence and antigenic variation in malaria; and C) Use of the HPV promoter, with a ribozyme targeted to a specific site near the translational start site of the E6 protein, a site known to be critical for expression of both the E6 and E7 proteins which are intimately involved in cervical carcinogenesis.

One example of the nucleic acid of the invention has the nucleotides in the sequence shown in the Sequence Listing as SEQ ID NO:1. This exemplary nucleic acid includes a probasin promoter, upstream from a sequence that encodes the 5' autocatalytically cleaving ribozyme having the sequence shown in SEQ ID NO:1, the ribosomal RNA binding site encoding DNA having the sequence shown in the Sequence Listing as SEQ ID NO:1 and the 3' autocatalytically cleaving ribozyme having the sequence shown in SEQ ID NO:1.

Alternatively, silent base substitutions in the promoter binding site and ribozyme encoding sequence can be made that express the same ribozyme in the same tissue. Thus, a nucleic acid having substantially the nucleotide sequence shown in SEQ ID NO:1, which encodes the ribozyme shown in SEQ ID NO: 1, is provided. The nucleic acid can vary based on the characteristics/definition of the promoter chosen, and will have 80%–99% sequence identity with SEQ ID NO:1, more preferably, it will have 90%–99% sequence identity with SEQ ID NO:1. Other modifications could include for example, changes (or deletion) of nucleotides inserted for cloning purposes (FIG. 2), which include −1 to −8, +69 to +76. In FIG. 3, the box includes extraneous nucleotides that are a function of cloning choices and, thus, can be modified. The unpaired bases can be any base, determined only by the cloning scheme chosen. If one of the bases of a pair is changed, the other must be changed in a complementary fashion. Furthermore, the ribozyme-coding sequence can be altered in ways that modify the ribozyme sequence, but do not effect the ribozyme's target RNA-specificity or negate its cleavage activity. For example, changes in the stem loop regions of the 5', 3', and internal ribozyme (FIG. 2) could be incorporated into other constructs while maintaining catalytic activity (Fedor and Uhlenbeck, 1990).

Synthesis of the Ribozyme Producing Construct

Typically, the RNA binding and core sequences are synthesized as reverse complementary oligonucleotides and are cloned into a vector that will allow production of the relevant RNA containing the ribozyme. The present ribozymes are prepared by synthesis of an oligonucleotide (5' GGA AGA TCT TTC AAA GAC TGA TGA CTC CGT GAG GAC GAA ACG AGG ATC AGA TCT TCC 3') and its reverse complement. The Bgl II site used in cloning is underlined. Following appropriate restriction digestion, in this particular case Bgl II, the double-stranded DNA oligonucleotide is cloned into the multiple cloning site within the parent vector (FIG. 1).

Functional Testing

Once sequenced, these ribozymes are functionally tested. The test can involve transcription of the ribozyme using one of the two possible bacterial promoters, in this case SP-6 or T-7, (in the presence of trace amounts of radioactivity) followed by evaluating the autocatalytic cleavage of the ribozyme by electrophoresis. Data from these tests are provided in the Examples.

Additional testing procedures encompass incubation of in vitro transcribed ribozymes with in vitro synthesized target RNA transcript or with cytoplasmic RNA preparations. Following incubations, RNAs are examined by standard Northern blot analyses to verify specific degradation of target RNA transcripts.

The triple-ribozyme that has been constructed can be further tested by subcloning it behind one of the tissue-specific promoters that will drive expression of the vector in a tissue-specific manner in the target. Data from these tests are provided in the Examples.

Finally, the triple-ribozyme experimental approach is further validated by doing in vivo studies in mice. Two such studies have been performed as described in the Examples. The first case used a control vector more easily monitored than the pol I ribozyme consisting of the probasin promoter driving expression of algal green fluorescent protein (pBGFT). This test vector is used to ascertain the effectiveness of our in vivo delivery system. A second experiment has also been carried out in which the pol I ribozyme is introduced. In both cases where either the triple ribozyme or the green fluorescent protein was introduced, the animals were euthanized at various time post operatively, autopsied, and various tissue were examined for activity of the vector by immunohistochemistry.

Delivery

The nucleic acids of the invention can be in a vector for delivering the nucleic acid to the site for expression of the ribozyme. The vector can be one of the commercially available preparations, such as the pGM plasmid (Promega). Vector delivery can be by liposome, using commercially available liposome preparations or newly developed liposomes having the features of the present liposomes. Other delivery methods can be adopted and routinely tested in methods taught herein. An example of a delivery method using liposomes is further described in the Examples.

The modes of administration of the liposome will vary predictably according to the disease being treated and the tissue being targeted. For lung (e.g., tuberculosis, cancer) and liver (e.g., hepatitis and cancer) which are both sinks for liposomes, intravenous administration is reasonable. For many other localized pathologic conditions including cancers, infections (e.g., hepatitis, cystitis, proctitis, cervicitis, etc.) as well as precancerous conditions, catheterization of an artery upstream from the organ is a preferred mode of delivery, because it avoids significant clearance of the liposome by the lung and liver. For lesions at a number of other sites (e.g., skin cancer, human papilloma virus infection, herpes (oral or genital) and precancerous cervical dysplasia), topical delivery is expected to be effective and may be preferred, because of its convenience.

Leukemias and other conditions such as malaria, may also be more readily treated by ex vivo administration of the ribozyme.

The liposomes may be administered topically, parenterally (e.g., intravenously), by intramuscular injection, by intraperitoneal injection, transdermally, excorporeally or the like, although IV or topical administration is typically preferred. The exact amount of the liposomes required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein. Generally, dosage will approximate that which is typical given in the Examples.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Topical administration can be by creams, gels, suppositories and the like. Ex vivo (excorporeal) delivery can be as typically used in other contexts.

Transgenic Animals

The invention provides a transgenic non-human animal, containing, in a germ or somatic cell, a nucleic acid comprising a target-specific promoter binding site upstream from a sequence encoding a 5' autocatalytically cleaving ribozyme sequence, a catalytic ribozyme comprising a target RNA-specific binding site and a 3' autocatalytically cleaving ribozyme sequence, wherein the animal expresses a ribozyme comprising a 5' autocatalytically cleaving ribozyme sequence, a catalytic ribozyme comprising a target RNA-specific binding site and a 3' autocatalytically cleaving ribozyme sequence.

The nucleic acid can be the nucleic acid shown in FIG. 1 and SEQ ID NO:1. Alternatively, silent base substitutions in the promoter binding site and ribozyme encoding sequence can be made that express the same ribozyme in the same tissue. For example, these substitutions can be as described above.

The transgenic non-human animal of the invention is useful, because the animal does not express a phenotype associated with the target RNA (e.g., with the protein it encodes). As used herein the term "phenotype" includes morphology, biochemical profiles (e.g., changes in amounts of RNA or protein expressed, etc.) and other parameters that are affected by the knockout. For example, cell death of otherwise healthy cells can be a measure of altered phenotype resulting from ribozyme expression.

Transformed Host Cells

The present ribozymes can be expressed in a transformed cell line. The transformed cell can be used to validate both the specificity of the ribozyme's expression and the specificity and cleavage activity against the target RNA. An example of such a screening function is described in the Examples.

Screening Methods

The transgenic animals and transformed host cells of the invention can be used in a method of screening a compound for its ability to cause the animal or host cell to express a phenotype associated with the target RNA. The method requires administering the compound to the animal/cell and assessing the compounds ability to cause expression of the phenotype. If the phenotype is restored, the compound is considered to be effective. For example an L-dopa functional knockout transgenic animal can be made and used to screen for drugs that restore an L-dopa associated phenotype.

Treating Proliferative Diseases

A method of treating a subject having a proliferative disease of a specific tissue is provided. The treatment is carried out by inhibiting cell proliferation in the specific tissue, and this is accomplished by administering to the subject a nucleic acid encoding a ribozyme that is targeted to an RNA that is essential to cell survival or replication, and containing a target-specific promoter binding sequence that is specific for the diseased tissue. The ribozyme encoded by the nucleic acid is expressed in the diseased tissue, production of an essential RNA in the tissue is inhibited, cell proliferation is inhibited in the tissue, cell death ensues and the proliferative disease treated.

The proliferative diseases that can be treated by the present method include almost all cancers for which a target-specific promoter exists, including, prostate, breast, colon, pancreatic, lung and liver.

For example, the invention provides a method of treating a subject having prostate cancer, comprising administering to the subject the nucleic acid shown in SEQ ID NO:1, whereby the ribozyme encoded by the nucleic acid is expressed in the prostate and the prostate cancer is treated.

Treating Viral Infection

A method of treating a viral infection in a subject, comprising administering to the subject a nucleic acid of the invention, wherein the encoded target RNA-specific binding site is specific for an RNA unique to the infectious agent, whereby the ribozyme encoded by the nucleic acid is expressed and the infectious agent is killed. Transcription can be driven using a virus specific promoter or a tissue-specific promoter which will selectively express the targeted ribozyme in virus-infected tissue, i.e., using the liver-specific albumin promoter for expression of a targeted ribozyme directed against hepatitis B virus.

In the context of determining anti-viral efficacy, ribozyme expressing cell lines can be compared with their ribozyme negative counterparts for their ability to support viral infection/replication/yield. In a manner similar to that described above, ribozyme expressing cell lines can be obtained and assayed; and in all cases the abilities of the ribozyme to prevent infection can be determined.

The present invention will be illustrated in further detail in the following non-limiting examples.

EXAMPLES

Analysis of Ribozyme Gene Therapy in Prostrate Cancer

This example presents the vectors and a novel strategy to utilizing prostate targeted expression of a hammerhead ribozyme to kill normal and neoplastic prostate epithelium. The ribozyme is a highly innovative, triple-ribozyme targeted to destroy cells by attacking essential RNA(s). The 5' and 3' ribozymes have been designed to undergo autocatalytic cleavage during transcription, freeing the internal ribozyme (at high levels) within the cells.

Intracellular expression of a hammerhead ribozyme, targeted towards an essential cellular RNA (such as RNA polymerase 1(A)), results in the death of the cell. If the ribozyme is targeted to a specific tissue in a constrained manner, then only cells in that tissue will be affected by expression of the ribozyme. Targeting selectively to prostate can be achieved via the rat probasin promoter (pb) (or the prostate specific antigen promoter). Because tissue-specific prostate targeting exists using the probasin promotor, delivery of vectors systemically or by direct introduction into the prostate will result in death of transfected prostate cancer cells with some collateral damage also being observed in the remaining normal prostate epithelium. Because of the rather unique specificity of the probasin promoter, no additional collateral damage is expected to be observed elsewhere in the body. This is also expected to be true for the prostate-specific antigen.

Examples of targets include the I(A) subunit of RNA polymerase I and II. Other internal targeted ribozymes are tested for in vitro and in vivo activity by the methods described.

Synthesis

The primary double ribozyme vector depicted in FIG. 1 was constructed. The two flanking ribozymes (bases 1 to 54 and 66 to 120) are capable of self-cleavage. A third ribozyme (FIG. 2) (bases 64 to 105) targeted to pol I mRNA is cloned between the flanking ribozymes. This internal ribozyme has 19 bases within two regions (TTCAAAGA-catalytic core-ACGAGGATCAG) that are anti-sense to the pol I message and interact by base pairing in regions with minimal secondary structures to effect cleavage.

The internal pol I ribozyme was prepared by synthesis of an oligonucleotide (5' GGA AGA TCT TTC AAA GAC TGA TGA CTC CGT GAG GAC GAA ACG AGG ATC AGA TCT TCC 3') (only the ribozyme sense strand is shown in its reverse complement). The Bgl II site used in cloning is underlined. Following appropriate restriction digestion with Bgl II the double-stranded oligonucleotide was cloned into the Bgl II site within the parent vector (FIG. 1).

Delivery

The prostate specific promoter, when coupled to the triple ribozyme construct, will be delivered to the prostate systemically via liposomes. Various routes of introduction into the blood vascular system (some bypassing the lung and liver) are evaluated as described. Orthotopic routes can also be utilized. The liposome vehicle is expected to be efficient enough to deliver the molecule to prostate cancer cells, because of a high degree of vascularization). Thus, curing or at least reducing tumor burden by this gene therapy approach is reasonably expected.

The following liposome preparations were used in these studies: (a) lipofectamine reagent (GIBCO BRL, Gaithersburg, Md.) is a polycationic lipid composed of a positively charged lipid, DOSPA, and the neutral lipid, DOPE, in a 3:1 molar ration; (b) the cationic lipid, DDAB, used in combination with DOPE at 2:1 or 0.6:1.0 ratios (Brunette et al. *Mol. Cell. Biol.* 14:2411–2418, 1994); and (c) DMRIE in combination with DOPE in a 1:1 molar ratio (Felgner et al. *Methods (Orlando)* 5:67–75, 1995), obtained from VICAL Corp. (San Diego, Calif.). Liposome reagents were stored at 4° C. prior to transfection.

Testing

Once sequenced, these ribozymes are functionally tested. The test mechanism involves transcription of the triple ribozyme using one of the two possible bacterial promoters, in this case SP-6 or T-7 present in the pCRII vector (Invitrogen, San Diego, Calif.), (in the presence of trace amounts of radioactivity) followed by evaluating the autocatalytic cleavage of the ribozyme by electrophoresis. This was carried out with the pol I ribozyme and cleavage was observed, i.e., first a 113 bp fragment was produced that included the internal targeting ribozyme and the 3' ribozyme, followed by the appearance of a 74 bp fragment containing the internal pol I ribozyme.

The ribozyme was subsequently tested by transient transfection of it into C3H10T ½ mouse fibroblast cells. This demonstrated that pol 1 RNA was degraded when triple ribozyme expression was induced. Thus, two phases of the activity of the molecule have been examined and demonstrated to occur. Autocatalytic cleavage of the cis ribozymes and functional degradation of pol I mRNA in trans occur as expected.

A subsequent step is to introduce the triple-ribozyme into a vector under the control of a tissue-specific promoter such as probasin or prostate specific antigen that will target expression in a tissue-specific manner. This was done by taking the Not 1 fragment containing the entire 3', 5' and internal ribozymes (FIG. 2) and subcloning it into a vector containing the probasin promoter region (−426 to +28 (Greenberg et al., 1994)). This promoter has been demonstrated to target gene expression to the prostate.

Vectors are tested in vivo in transgenic mice expressing the triple ribozyme anti-pol I construct. Transgenic mice are generated by standard pronuclear injection as described in Hogan (Manipulating the mouse embryo: a laboratory manual, Cold Spring Harbor, N.Y. 1986). Prior to injection, constructs are separated from vector DNA by restriction digestion (Hind III and Sac II) of the plasmid, followed by sucrose gradient fractionation. Isolated constructs are dialyzed against 10 mm tris ph 8.0, 0.1 mm EDTA before injection. In these mice, once probasin expression becomes apparent at the 3–5 week stage of post natal development destruction of prostate epithelium is expected to occur. The efficiency of generating transgenic mice is 10–15% with twenty-six mice delivered, i.e. 2–3 transgenic mice are predicted. Another way to verify the present ribozymes' functionality is to introduce the vector into tissue culture, e.g., human PC3 prostate cancer cells, and observe cell death in response to activation of the ribozyme. C3H10T ½ mouse fibroblasts have been confirmed as sensitive to the pol I triple ribozyme.

Further validation of this gene therapy approach is obtained through in vivo studies. Two such studies have been performed. In the first case, a control vector, more easily monitored than the pol I ribozyme, which consists of the probasin promoter driving expression of the algal green fluorescent protein was used to ascertain the effectiveness of the in vivo liposomal delivery system. The procedure involves mice that are anesthetized and prepared by a surgical procedure to expose the descending aorta. A 30 gauge catheter is placed in the descending aorta followed by introduction of 300 µg vector/kilogram body weight (vector: liposome ratio of 10 µg/40 µl). The results verify that expression of the green fluorescent protein occurs in dorsolateral prostate epithelium but not in the lung (a normal target of liposomes). Further studies determine if expression is observed in liver and other tissue including the kidney, adrenal gland and the brain. A second experiment has also been carried out in which the pol I ribozyme was introduced in vivo using the same method described above. In both cases where either the triple ribozyme or the green fluorescent protein was introduced, animals were euthanized at various time post operatively, autopsied, and tissues were examined for activity of the vector by immunohistochemistry. There was evidence of some apoptotic cell death in prostate epithelium at seven days following administration.

In vivo studies are conducted in transgenic mice bearing prostate tumors. Tumors are induced by probasin directed expression of genes such as EcoR1 (a restriction enzyme), cfos (a proto-oncogene), or a modified version of lamin (a nuclear matrix molecule). Administration of the ribozyme is as described above Target Choice Various molecules have been chosen for targeting. The first is RNA polymerase 1(A). This represents an excellent target, because it is an abundant RNA. If there is a leakiness (low levels of transcription) of the probasin promoter in other than prostate cells, they are predicted to survive the presence of limited levels of the Pol I ribozyme. Other potential targets will be examined including phosphofructokinase (ribozyme targets nt 178, 121, or 162 depending on tissue involved), RNA pol II subunit 14.4 kd (ribozyme targets nt 83 or 884), mRNA pol II 140 kd subunit (ribozyme targets nt 204), and RNA pol II 23 kd subunit (ribozyme targets nt 143)

Another potential target of interest is the 70 kD subunit of replication protein A. It is needed for formation of DNA replication centers/foci, so it should disrupt DNA replication without danger of introducing errors. The sequence reference is Kim, et al., *Mol. Cell. Biol.* 12:3050–3059, 1992.

Ribozyme Gene Therapy in Parasitic Infection

The methods described above are applicable to the present context, except where specified. For example, The administration mode will be different for parasitic infection than for prostate cancer and will depend upon tissue site.

For malaria (*Plasmodium falciparum*) the EMP-1 proteins, which are necessary for cytoadherence and present a problem because they cause rapid antigenic variation, are targeted. Specifically, highly conserved GTCs in exon II are targeted. Pertinent EMBL accession numbers are L42246, L42244, L42245, L42247, L40600–L40609, L42636. See Smith, J. et al. *Cell* 82:101–110, 1995, and Su, X. et al. *Cell* 82:89–100, 1995. A promoter active in red blood cells can be used and treatment also could be extracorporeal.

Ribozyme Gene Therapy in Bacterial Infection

The methods described above are applicable to the present context, except where specified. For example, The administration mode will be different for bacterial infection than for prostate cancer, and will depend on the targeted tissue.

For Mycobacterium tuberculosis, a transcribed fragment which is essential for cell entry will be targeted. The EMBL accession number is X70901. See Arruda, S. et al. *Science* 261:1454–1457, 1993. The target will be near the N-terminus of the open reading frame coding for the 52 kD protein, from the 1535 bp fragment.

reference is Galibert, et al., Nature 281, 646–650, 1979. Expression could be driven by the albumin promoter and IV administration should be highly effective.

While the foregoing invention has been described in some detail for purposes of clarity and understanding, it will be appreciated by one skilled in the art from a reading of this disclosure that various changes in form and detail can be made without departing from the true scope of the invention and appended claims.

Throughout this application various publications are referenced within parentheses. The disclosures of these publications in their entireties are hereby incorporated by reference into this application in order to more fully describe the state of the art to which this invention pertains.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 185 base pairs
( B ) TYPE: nucleic acid
( C ) STRANDEDNESS: double
( D ) TOPOLOGY: linear ( i i ) MOLECULE TYPE: oligonucleotide ( x i ) SEQUENCE DESCRIPTION: SEQ ID NO:1:

```
GCGGCCGCTC GAGCTCTGAT GAGTCCGTGA GGACGAAACG GTACCCGGTA CCGTCAGCTC   60
GAGCTCAGAT CTTTCAAAGA CTGATGACTC GCTGAGGACG AAACGAGGAT CAGATCTGGA  120
TCCGTCGACG GATCTAGATC CGTCCTGATG AGTCCGTGAG GACGAAACGG ATCTGCAGCG  180
GCCGC                                                              185
```

Ribozyme Gene Therapy in Viral Infection

The methods described above are applicable to the present context, except where specified. For example, the administration mode will be different for viral infection than for prostate cancer.

Human papillomavirus type 16 E6 and E7 proteins are translated from a bicistronic mRNA. Antisense oligonucleotides to the translational start site of E6 inhibit synthesis of both E6 and E7. The target will be a GTT, cleaving at nt 108 (Tan, et al., *J. Gen. Virol.* 75:2663–2670, 1994). Original numbering is from Seedort, et al., *Virology* 145:181–185, 1985. IV and topical administration should be an effective combination. Topical administration should be effective for dysplastic/precancerous lesions.

Hepatitis B virus is a partially single-stranded DNA virus, and it is now thought that integration of the viral genome is not the critical incident. Rather, the viral genome is made into an extended RNA intermediate, which is then reverse transcribed into DNA. A target with multiple advantage has been chosen. It will cut the viral RNA pregenome in the first place, and its located in both the S (envelope) and polymerase/reverse transcriptase domains. The cut is at a GTC, after nt 438 in the HBV subtype ayw. The EMBL accession number is X02496, and the original sequence

What is claimed is:

1. A DNA comprising a tissue-specific promoter upstream from a sequence encoding a triple ribozyme, comprising a) a 5' autocatalytically cleaving ribozyme, b) a trans-acting ribozyme that binds and cleaves a selected RNA and c) a 3' autocatalytically cleaving ribozyme.

2. The nucleic acid of claim 1, wherein the tissue-specific promoter is the probasin promoter.

3. The nucleic acid of claim 1, wherein the nucleic acid encoding the 5' autocatalytically cleaving ribozyme has the sequence of nucleotides 9–62 set forth in the Sequence Listing as SEQ ID NO:1.

4. The nucleic acid of claim 1, wherein the nucleic acid encoding the 3' autocatalytically cleaving ribozyme has the sequence of nucleotides 119–172 set forth in the Sequence Listing as SEQ ID NO:1.

5. The nucleic acid of claim 1, wherein the nucleic acid encodes a trans-acting ribozyme comprising, a site that binds to an RNA sequence unique to ribosomal RNA polymerase I(A).

6. The nucleic acid of claim 5, wherein the nucleic acid has the sequence of nucleotides 72–113 set forth in the Sequence Listing as SEQ ID NO:1.

7. The nucleic acid of claim 1, comprising the sequence set forth in the Sequence Listing as SEQ ID NO:1.

8. The nucleic acid of claim 1, consisting of the nucleotides in the sequence set forth in the Sequence Listing as SEQ ID NO:1.

9. The nucleic acid of claim 1 in a vector.

10. The nucleic acid of claim 2 in a vector.

11. The nucleic acid of claim 3 in a vector.

12. The nucleic acid of claim 4 in a vector.

13. The nucleic acid of claim 5 in a vector.

14. The nucleic acid of claim 6 in a vector.

15. The nucleic acid of claim 7 in a vector.

16. The nucleic acid of claim 8 in a vector.

* * * * *